United States Patent [19]

Hardy et al.

[11] 4,294,776
[45] Oct. 13, 1981

[54] PROCESS FOR THE PURIFICATION OF ORGANIC SOLUTIONS OF PERCARBOXYLIC ACIDS

[75] Inventors: Nicolas Hardy; Georges Dancot, both of Jemeppe-sur-Sambre, Belgium

[73] Assignee: Propylox (Societe Anonyme), Brussels, Belgium

[21] Appl. No.: 145,836

[22] Filed: May 1, 1980

[30] Foreign Application Priority Data

May 4, 1979 [FR] France .................. 79 11234

[51] Int. Cl.³ .......................................... C07C 179/10
[52] U.S. Cl. ............................................. 260/502 R
[58] Field of Search .................................. 260/502 R

[56] References Cited

U.S. PATENT DOCUMENTS

| | | | |
|---|---|---|---|
| 4,087,454 | 5/1978 | Prescher et al. | 260/502 R |
| 4,088,676 | 5/1978 | Hofen et al. | 260/502 R |
| 4,101,570 | 7/1978 | Krüger et al. | 260/502 R |
| 4,160,778 | 7/1979 | Hildon et al. | 260/502 R |
| 4,177,196 | 12/1979 | Hildon et al. | 260/502 R |

FOREIGN PATENT DOCUMENTS 808108 11/1973 Belgium .
2379520 4/1978 France .

*Primary Examiner*—Werren B. Lone
*Attorney, Agent, or Firm*—Spencer & Kaye

[57] ABSTRACT

Organic solutions of percarboxylic acids are subjected to a wash by means of a dilute aqueous solution containing from 35 to 60% by weight of sulphuric acid, which if appropriate, is preceded by a preliminary wash by means of a concentrated aqueous solution containing more than 65% by weight of sulphuric acid.

10 Claims, 2 Drawing Figures

PROCESS FOR THE PURIFICATION OF ORGANIC SOLUTIONS OF PERCARBOXYLIC ACIDS

BACKGROUND OF THE INVENTION

The present invention relates to a process for the purification of organic solutions of percarboxylic acids and more particularly of organic solutions of percarboxylic acids obtained by reaction of the corresponding carboxylic acids or carboxylic anhydrides with hydrogen peroxide in the presence of a catalyst such as sulphuric acid.

It is known to manufacture organic solutions of percarboxylic acids by reacting an aqueous solution of sulphuric acid and hydrogen peroxide with an organic solution of the corresponding carboxylic acid in a liquid-liquid extraction device and washing the resulting organic solution of the peracid by means of a very concentrated aqueous solution of sulphuric acid (French Patent Application No. 78/12,254, filed on Apr. 24, 1978 in the name of INTEROX CHEMICALS LTD). The object of this purification is to reduce the hydrogen peroxide content of the organic solution obtained. However, it has the disadvantage of producing an organic solution of the peracid which has a rather high sulphuric acid content, and this can encourage corrosion and side-reactions during the subsequent use of these organic solutions, for example for the epoxidation of olefins.

It is also known to manufacture solutions of percarboxylic acids in benzene by reacting a carboxylic acid with hydrogen peroxide in an aqueous phase in the presence of an acid catalyst, extracting the peracid from the resulting mixture by means of benzene and washing the resulting organic solution of the peracid with water or with sulphuric acid diluted to 25% (Belgian Pat. No. 808,108, filed on Nov. 30, 1973 in the name of DEGUSSA). This process has the disadvantage of giving an organic solution of the peracid in which the water content is too high, which again encourages corrosion and side-reactions during subsequent use of these organic solutions, for example for the epoxidation of olefins.

SUMMARY OF THE INVENTION

It is the object of the invention to provide a process of purification which makes it possible to obtain organic solutions of percarboxylic acids which only contain negligible amounts of water, of hydrogen peroxide and of sulphuric acid, and hence which do not suffer from the abovementioned disadvantages. The process according to the invention has the additional advantage that it is particularly easy to carry out. Furthermore, it does not require a high energy consumption, and only entails slight losses of hydrogen peroxide. Finally, the separation of the organic solution of the peracid from the wash solutions employed is easy even if heavy organic solvents, such as chlorinated hydrocarbons, are used.

To this effect, the invention relates to a process for the purification of organic solutions of percarboxylic acids in an inert organic solvent, the solutions originating from the manufacture of percarboxylic acids by reaction of the corresponding carboxylic acids or carboxylic anhydrides with hydrogen peroxide in the presence of catalysts, in which the solutions to be purified are subjected to a wash by means of a dilute aqueous solution containing from 35 to 60% by weight of sulphuric acid.

Good results have been obtained by using, in accordance with the invention, dilute aqueous solutions containing from 40 to 55% by weight of sulphuric acid. The best results have been obtained by using dilute aqueous solutions containing about 50% by weight of sulphuric acid.

According to a preferred embodiment of the invention, the washing of the organic solution of the peracid by means of the dilute aqueous solution is preceded by a preliminary wash by means of a concentrated aqueous solution containing more than 65%, and preferably from 70 to 97%, by weight of sulphuric acid.

DETAILED DESCRIPTION OF THE INVENTION

Figure 1:
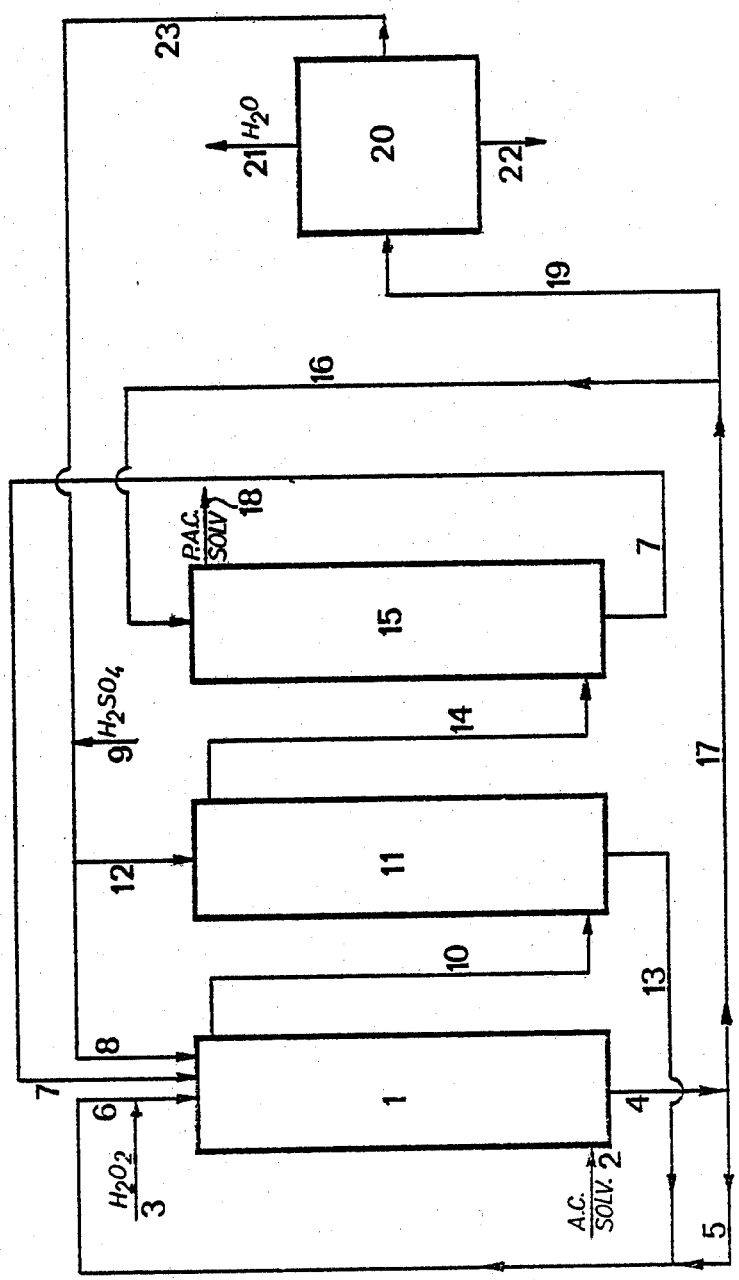
FIGS. 1 and 2 are schematic diagrams of apparatuses which can be used to continuously carry out the process of the present invention.

The aqueous solutions of sulphuric acid which are used according to the invention and may be used for the preliminary wash can contain, in addition to sulphuric acid and water, small amounts of products such as the desired percarboxylic acid and the corresponding carboxylic acid. These products are present in varying amounts which in general do not exceed 20%, and most commonly are less than 15%, of the weight of the solution. The solutions may also contain small amounts of hydrogen peroxide; in that case, care is generally taken that the amount of hydrogen peroxide present in the solution does not exceed 5% of the weight of the solution, so as to avoid the re-extraction of the hydrogen peroxide by the organic solution. The presence of small amounts of hydrogen peroxide in the aqueous solutions of sulphuric acid has the advantage that it reduces corrosion of the installation. This advantageous effect is achieved even with concentrations as low as 0.01% by weight of hydrogen peroxide in the aqueous solution. However, it is preferred that the concentration should exceed 0.1% by weight. Good results have been obtained with aqueous solutions of sulphuric acid which may contain up to 2%, of the weight of solution, of hydrogen peroxide.

The process according to the invention is particularly suitable for the purification of organic solutions of percarboxylic acids obtained by reaction of the corresponding carboxylic acids or carboxylic anhydrides with hydrogen peroxide in the presence of sulphuric acid as the catalyst, and simultaneous or subsequent extraction of the peracids formed by means of the inert organic solvent. In such a process the products obtained at the end of the manufacture of the peracid are in effect, on the one hand, an organic solution of the peracid to be purified and, on the other hand, a dilute aqueous solution which contains sulphuric acid and may contain small amounts of unconverted hydrogen peroxide and of extracted percarboxylic acid and carboxylic acid. This dilute aqueous solution of sulphuric acid can advantageously be employed, at least in part, for the wash according to the invention, if the latter follows a preliminary wash carried out with a concentrated aqueous solution of sulphuric acid. The sulphuric acid content of the dilute aqueous solution is adjusted, if necessary, to the desired value by adding water or concentrated sulphuric acid to the acid aqueous solution obtained at the end of the manufacture of the peracid.

In this case, the organic solution of peracid is first of all subjected to a preliminary wash by means of a concentrated aqueous solution of sulphuric acid and the aqueous solution of sulphuric acid collected at the end of the preliminary wash can advantageously be recycled to the manufacture of the peracid. The organic solution of peracid obtained from the preliminary wash is then washed in accordance with the invention by means of the dilute aqueous solution of sulphuric acid obtained at the end of the manufacture of the peracid. As regards the part of the dilute aqueous solution of sulphuric acid which is collected at the end of the manufacture of the peracid and has not been used, it can be concentrated and the concentrated aqueous solution of sulphuric acid thus obtained can be employed to carry out the reaction of the hydrogen peroxide with the corresponding carboxylic acids or carboxylic anhydrides.

The embodiment of the process according to the invention described above is very particularly suitable for the purification of organic solutions of percarboxylic acids obtained in accordance with the process described in the abovementioned French Patent Application No. 78/12,254, where the manufacture of the peracid and its extraction by means of the inert organic solvent take place simultaneously.

A preferred variant of this embodiment accordingly consists in applying the process according to the invention to the purification of organic solutions of percarboxylic acids obtained by formation of the peracids and their simultaneous extraction by the inert organic solvent, adding a topping-up amount of hydrogen peroxide and, if necessary, of sulphuric acid to the concentrated aqueous solution obtained from the preliminary wash, and employing the solution thus obtained for carrying out the reaction of the hydrogen peroxide with the corresponding carboxylic acids or carboxylic anhydrides.

In the embodiment described above, a concentrated aqueous solution of sulphuric acid containing less than 1% by weight of hydrogen peroxide is preferably employed for the preliminary wash.

The amounts of the aqueous solutions of sulphuric acid to be employed for the wash, and for any preliminary wash, can vary.

The dilute aqueous solution is in general employed in amounts of 0.01 to 100%, and preferably of 0.1 to 10%, of the weight of the organic solution of peracid which is to be treated.

In general, the amount of dilute aqueous solution of sulphuric acid employed is such that the concentration of sulphuric acid in the aqueous solution obtained after washing with this dilute solution is between 35 and 70% by weight. Good results are obtained if this concentration is between 40 and 65%.

The concentrated solution is in general employed in an amount of 0.1 to 200%, preferably of 1 to 100%, of the weight of the organic solution of peracid which is to be treated.

The temperature at which the wash of the organic solution of the peracid is carried out is in general rather low, most commonly between 263 and 303 K and preferably between 268 and 293 K. The use of low temperatures makes it possible to reduce the water content of the organic solution of the peracid.

The temperature at which the preliminary wash is carried out appears in itself not to be critical. In general, temperatures of between 263 and 323 K, and preferably between 268 and 303 K, are used.

The washes may be carried out in accordance with the various techniques which are in themselves known. Thus, the organic solution of the peracid can be brought into contact with the solution of sulphuric acid in liquid-liquid extraction devices such as mixing-decanting vessels, which may or may not be combined with coalescing devices, or such as counter-current or co-current extraction columns. It is also possible to use a combination of one or more mixing-decanting vessels, of one or more columns of the same type or of different types, or of several of these devices. Good results are obtained by using counter-current extraction columns or batteries of mixing-decanting vessels, so arranged as to produce a counter-current effect.

The apparatus used to carry out the washes is made from corrosion-resistant materials. Thus it is possible to use apparatus of which the walls in contact with the organic solution of the peracid and with the solutions of sulphuric acid are made from stainless steel, from enamelled steel, or from INCONEL, HASTELLOY, INCOLOY, MONEL, NIMONIC, NI-RESIST and CHLORIMET alloys.

The process according to the invention can be applied to the purification of organic solutions containing various types of percarboxylic acids, either as individual compounds or as mixtures. Thus, it can be used to purify organic solutions of monopercarboxylic acids or polypercarboxylic acids. The process is particularly suitable for the purification of organic solutions of percarboxylic acids containing from 1 to 10 carbon atoms whether these be aliphatic, alicyclic or aromatic percarboxylic acids, such as performic acid, peracetic acid, chloroperacetic acids, perpropionic acid, chloroperpropionic acids, perbutanoic acid, percaproic acid, permaleic acid, perheptanoic acid, perbenzoic acid, percyclohexanoic acid, perpelargonic acid and perphthalic acids. Particularly advantageous results are obtained in the purification of organic solutions of peracetic acid and perpropionic acid.

The process according to the invention can be applied to the purification of organic solutions of percarboxylic acids in various types of inert solvents. In general, solvents which are sparingly soluble in water and in sulphuric acid are employed; their solubility in these products is in general less than 1% by weight. They are selected from amongst the solvents which are inert towards the constituents of the system under the washing conditions. These solvents are in general chosen from amongst carboxylic acid esters, ethers, halogenated hydrocarbons, unsubstituted hydrocarbons, hydrocarbons substituted by nitro groups, nitric acid esters, non-acidic esters of carbonic acid and of phosphoric acid, nitriles and mixtures of these.

As halogenated hydrocarbons which in general are very suitable there may be mentioned aromatic, aliphatic and alicyclic halogenated hydrocarbons containing from 1 to 8 carbon atoms in their molecule and substituted by at least one halogen preferably selected from amongst chlorine, fluorine and bromine. Halogenated hydrocarbons which are particularly suitable are carbon tetrachloride, chloroform, methylene chloride, chloroethane, dichloroethanes, trichloroethanes, tetrachloroethanes, pentachloroethanes, trichlorotrifluoroethanes, trichloroethylene, tetrachloroethylene, monochloropropanes, dichloropropanes, trichloropropanes, tetrachloropropanes, monochlorinated or polychlorinated butanes, methylpropanes, pentanes and hexanes, monochlorobenzene, dichlorobenzenes and chlorotoluenes.

Amongst all these chlorinated hydrocarbons, the lower chlorinated hydrocarbons containing from 1 to 3 carbon atoms are in general preferred.

As carboxylic acid esters which are generally very suitable there may be mentioned the aliphatic, alicyclic or aromatic esters of monocarboxylic or polycarboxylic acids with monohydric or polyhydric alcohols, containing from 2 to 20, and preferably from 3 to 10, carbon atoms in the molecule. Amongst these esters, the following are particularly suitable: isopropyl, propyl, butyl, isobutyl, sec.-butyl, tert.-butyl, amyl, isoamyl and sec.-amyl formates and acetates, methyl, ethyl, propyl, isopropyl, butyl, isobutyl and isoamyl monochloroacetates, dichloroacetates, propionates, butyrates and isobutyrates, methyl, ethyl and propyl valerates, isovalerates and caproates, methoxyethyl, ethoxyethyl and cyclohexyl acetates, methyl pivalate, diethyl phthalate, diethyl adipate and di-n-butyl phthalate.

As ethers which in general are very suitable there may be mentioned the symmetrical or asymmetrical aliphatic or alicyclic ethers containing from 3 to 20, and preferably from 4 to 12, carbon atoms, such as diethyl ether, 2,2'-dichlorodiethyl ether, methyl propyl ether, ethyl propyl ether, butyl ethyl ether, tert.-butyl ethyl ether, tert.-amyl methyl ether, diisopropyl ether, dipropyl ether, dibutyl ether, ethyl hexyl ether, diisobutyl ether, dioxane and methylal.

As unsubstituted hydrocarbons which in general are very suitable there may be mentioned the aliphatic, aromatic or alicyclic hydrocarbons containing from 5 to 14 carbon atoms, such as benzene, toluene, xylene, pentane, hexane, heptane, octane, 2,5-dimethyl-hexane, decane, cyclohexane, methylcyclohexane, tetralin or aliphatic hydrocarbon mixtures, such as petroleum ether.

As hydrocarbons substituted by nitro groups, which in general are very suitable, there may be mentioned the aromatic, aliphatic or alicyclic hydrocarbons containing from 1 to 10, preferably from 1 to 8, carbon atoms, such as the nitropropanes, nitrobenzene and nitrocyclohexane.

As carbonic acid esters which in general are very suitable there may be mentioned the aliphatic esters containing from 3 to 9 carbon atoms in the molecule, such as dimethyl, diethyl, diisobutyl, dibutyl, di-tert.-butyl, dipropyl and diisopropyl carbonate. Nitric acid esters which in general are very suitable are those selected from amongst the aliphatic esters containing from 1 to 5 carbon atoms in the molecule, such as methyl, propyl, butyl and isoamyl nitrate.

Very suitable phosphoric acid esters are those corresponding to the formula

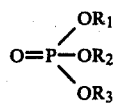

in which $R_1$, $R_2$ and $R_3$ are identical or different and represent alkyl, aryl, arylalkyl or alkylaryl groups, the groups being such that the molecule contains from 3 to 30 carbon atoms. By way of specific examples of phosphates there may be mentioned trimethyl, tributyl, trioctyl and dioctyl phenyl phosphate.

As nitriles which in general are very suitable there may be mentioned the nitriles containing from 2 to 10 carbon atoms in the molecule, such as benzonitrile.

The solvents most frequently employed in the organic solutions of peracetic acid and of perpropionic acid are benzene, toluene, cyclohexane, decane, heptane, petroleum ether, 1,2-dichloropropane, 1,1,2,2-tetrachloroethane, 1,2-dichloroethane, pentachloroethane, trichloroethylene, tetrachloroethylene, nitrobenzene, chlorobenzene, cyclohexyl chloride, diethyl phthalate, di-n-butyl phthalate, ethyl propionate, di-n-propyl ether and tributyl phosphate. Particularly good results are obtained with 1,2-dichloroethane, 1,2-dichloropropane, benzene and mixtures of these.

The organic solutions of percarboxylic acids which are to be purified can contain varying amounts of percarboxylic acids. In general, the peracid content of the solutions is greater than 1% and preferably greater than 2% by weight. Where relevant, the maximum concentration of peracid should not exceed the limit of solubility of the peracid in the solvent, nor the concentration corresponding to the explosive limit of the solution. The organic solutions of peracids to be purified in general contain from 2 to 50%, and most commonly from 4 to 40%, by weight of peracids.

The organic solutions of percarboxylic acids to be purified can also contain varying amounts of the corresponding carboxylic acid. These acids are in general present in amounts of between 0.1 and 60% and most commonly of between 0.5 and 50% of the weight of the solutions.

The impurities which are essentially eliminated by the process according to the invention are hydrogen peroxide, water and sulphuric acid. These impurities are present in varying amounts in the solutions to be purified. In general, the organic solutions of peracids contain up to 1% by weight of hydrogen peroxide, up to 1% by weight of water and up to 1% by weight of sulphuric acid.

The process according to the invention makes it possible to obtain purified organic solutions of percarboxylic acids which are particularly suitable for the epoxidation of olefins such as of propylene, allyl chloride, allyl alcohol and styrene.

Figure 2:
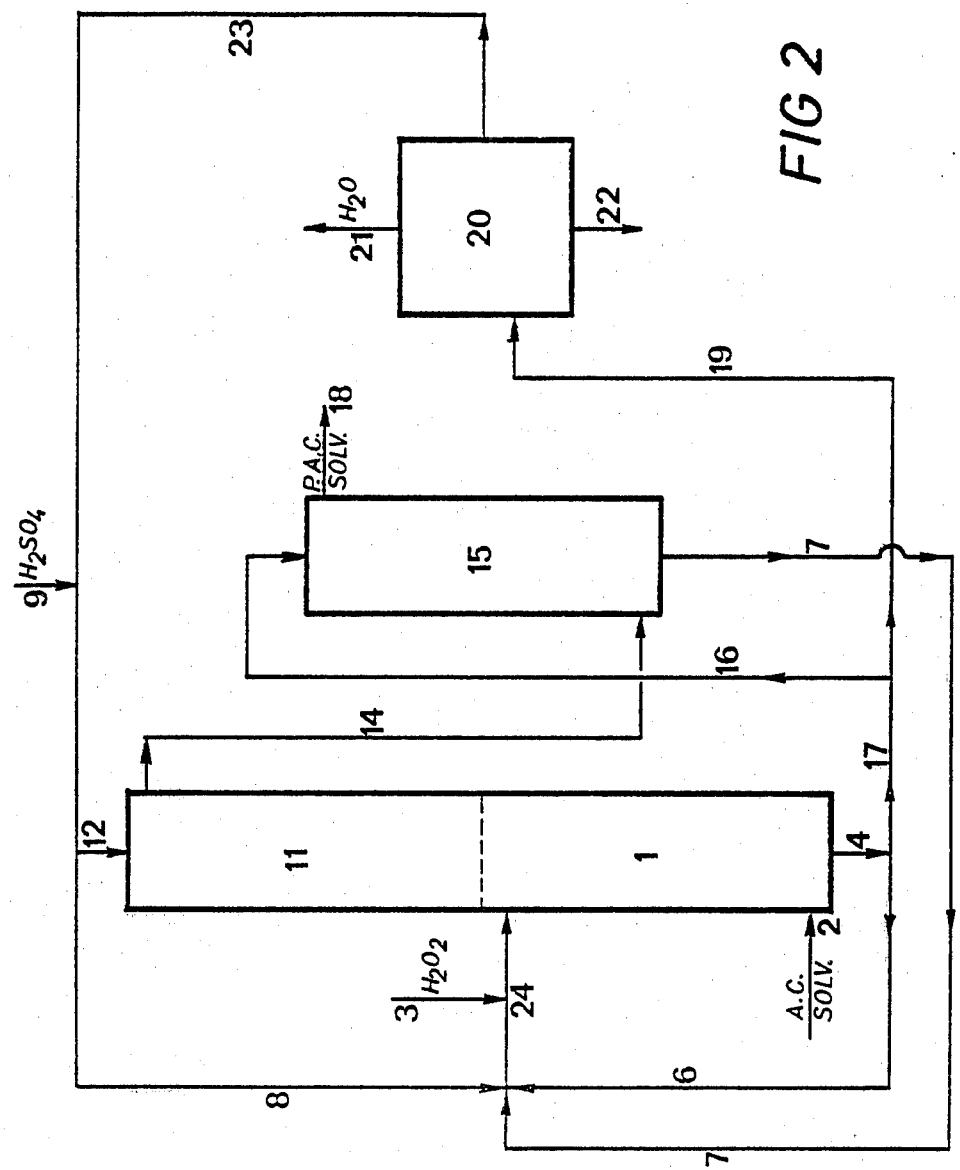

The process according to the invention can be carried out continuously in apparatus such as those shown schematically in FIGS. 1 and 2 of the attached drawings, which relate to specific practical embodiments.

According to the process shown in FIG. 1, a solution of carboxylic acid (A.C.) in an inert organic solvent (SOLV.) is introduced into the reactor 1 through line 2. A fresh aqueous solution of hydrogen peroxide is introduced, through line 3, into one of the streams of sulphuric acid fed into the reactor, namely either into line 6 (shown in FIG. 1) or into line 8 (not shown) or into line 7 (not shown). The dilute aqueous solution of sulphuric acid collected at the bottom of the reactor through line 4 can be partially recycled to the reactor 1 through lines 5 and 6. Recycled concentrated sulphuric acid solutions are fed to the reactor through lines 7 and 8 and a topping-up amount of fresh concentrated sulphuric acid is introduced through line 9.

The organic solution of peracid which is to be purified, and which contains hydrogen peroxide, leaves the reactor 1 through line 10 and enters the preliminary wash zone 11. The concentrated sulphuric acid solution used for the wash is introduced into the preliminary wash zone 11 through line 12. The sulphuric acid solution collected at the outlet of the wash zone 11 passes through line 13 and is recycled to the reactor 1 through line 6. At the outlet of the preliminary wash zone 11 an organic solution of peracid, substantially free from dissolved hydrogen peroxide but containing sulphuric acid, is collected. This organic solution, optionally after addition of a portion of solvent (not shown), is fed through line 14 into the wash zone 15, into which a part of the dilute aqueous solution of sulphuric acid collected at the bottom of the reactor 1 through lines 4 and 17 is also introduced, through line 16. The organic solution of purified peracid (P.A.C.) is collected through line 18. The aqueous sulphuric acid solution which has left the wash zone 15 is recycled to the reactor 1 through line 7.

A part of the dilute aqueous sulphuric acid solution collected at the bottom of the reactor 1 is fed through lines 4, 17 and 19 into a concentration zone 20, water being removed through line 21; a means of draining can be provided, for example through line 22. The concentrated aqueous solution of sulphuric acid is partially fed to the reactor 1 through lines 23 and 8 and partially to the preliminary wash zone through lines 23 and 12.

FIG. 2 shows a variant of the process shown in FIG. 1, in which the preliminary wash zone 11 and the reactor are superposed. The sulphuric acid solutions coming respectively from the concentration zone 20 through lines 23 and 8, from the wash zone 15 through line 7 and from the reaction zone 1 through lines 4 and 6 are fed simultaneously into the reaction zone 1 through line 24, at the same time as the hydrogen peroxide introduced through line 3. In such a device, it is also possible to arrange for the hydrogen peroxide to be introduced in stages along the reaction zone. This arrangement is not shown in the figure.

In order to allustrate the invention, without however limiting its scope, a practical example of an embodiment is given below.

EXAMPLE

Manufacture of a solution of perpropionic acid in 1,2-dichloropropane

The apparatus is similar to that shown schematically in FIG. 1.

The preliminary wash zone 11 consists of a liquid-liquid counter-current extraction column.

The wash zone 15 comprises a mixer, followed by a cooler at 273 K and, finally, a coalescing-decanting vessel.

The composition of the streams of material in the two wash zones is given in Table 1 below, in kg/h.

TABLE 1

| | Aqueous solution of sulphuric acid | | | Organic solution of the peracid | | | |
|---|---|---|---|---|---|---|---|
| | Preliminary wash | Wash | | Preliminary wash | | Wash | |
| | entering line 12 | entering line 16 | leaving line 7 | entering line 10 | leaving line 14 | entering line 14 | leaving line 18 |
| Propionic acid | — | 0.5 | 0.71 | 55.3 | 49.4 | | 49.7 |
| Perpropionic acid | — | 0.07 | 0.66 | 53.3 | 50 | | 48.6 |
| 1,2-Dichloropropane | — | — | — | 275.2 | 275.2 | | 275.2 |
| Water | 6.81 | 2.85 | 2.81 | 1.4 | 0.6 | | 0.63 |
| $H_2O_2$ | 0.02 | 0.05 | 0.28 | 1.1 | 0.34 | | 0.34 |
| $H_2SO_4$ | 20.6 | 3.46 | 4.75 | 0.2 | 1.5 | | 0.11 |
| $H_2SO_5$ | 0.07 | 0.07 | 0.19 | — | — | | — |

The composition in % by weight of the organic solution of perpropionic acid in 1,2-dichloropropane before and after purification is shown in Table 2 below.

TABLE 2

| | Composition of the organic solution of the peracid, % by weight | | |
|---|---|---|---|
| | before purification | After the preliminary wash with 75% strength $H_2SO_4$ | After the wash with 50% strength $H_2SO_4$ |
| Propionic acid | 14.3 | 13.1 | 13.3 |
| Perpropionic acid | 13.8 | 13.3 | 13.0 |
| $H_2O$ | 0.36 | 0.16 | 0.17 |
| $H_2O_2$ | 0.285 | 0.09 | 0.09 |
| $H_2SO_4$ | 0.052 | 0.4 | 0.03 |

What is claimed is:

1. In a process for the purification of an organic solution of a percarboxylic acid in an inert organic solvent, the solution originating from the manufacture of a percarboxylic acid by reaction of the corresponding carboxylic acid or carboxylic anyhydride with hydrogen peroxide in the presence of a catalyst, under conditions sufficient to produce said percarboxylic acid, the improvement comprising subjecting the solution to be purified to a wash at a temperature of 263° to 303° K., by means of a dilute aqueous solution containing from 35 to 60% by weight of sulphuric acid.

2. Process according to claim 1, wherein the wash by means of the dilute aqueous solution is preceded by a preliminary wash by means of a concentrated aqueous solution containing more than 65% by weight of sulphuric acid.

3. Process according to claim 2, wherein the catalyst comprises sulphuric acid, the percarboxylic acid formed is extracted by means of the inert organic solvent, and the dilute aqueous solution of sulphuric acid originating from the extraction is used for the wash.

4. Process according to claim 3, which is applied to the purification of an organic solution of a percarboxylic acid obtained by formation of said percarboxylic acid and its simultaneous extraction by the inert organic solvent, wherein a topping-up amount of hydrogen peroxide is added to the concentrated aqueous solution obtained from the preliminary wash and wherein the solution thus obtained is employed for carrying out the reaction of the hydrogen peroxide with the corresponding carboxylic acid or carboxylic anhydride.

5. Process according to claim 3 or 4, wherein only a part of the dilute aqueous solution of sulphuric acid originating from the extraction is used for the wash and the other part is concentrated and the solution thus obtained is employed for carrying out the reaction of the hydrogen peroxide with the corresponding acids or anhydrides.

6. Process according to claim 1 or 2, wherein the wash by means of the dilute aqueous solution of sulphuric acid is carried out at a temperature of between 268 and 293 K.

7. Process according to claim 1 or 2, which is applied to the purification of an organic solution of a percarboxylic acid in a solvent selected from the group consisting of 1,2-dichloroethane, 1,2-dichloropropane, benzene and mixtures of these.

8. Process according to claim 1 or 2, which is applied to purification of an organic solution of a percarboxylic acid selected from the group consisting of peracetic acid and perpropionic acid.

9. Process according to claim 4, wherein a topping-up amount of sulphuric acid is additionally added to the concentrated aqueous solution obtained from the preliminary wash.

10. Process according to claim 1 or 2, wherein said dilute aqueous solution contains from 40 to 55% by weight of sulphuric acid.

* * * * *